(12) United States Patent
Guo et al.

(10) Patent No.: US 12,570,723 B2
(45) Date of Patent: *Mar. 10, 2026

(54) RECOMBINANT HUMANIZED COLLAGEN TYPE III ALPHA-1, AND EXPRESSION VECTOR AND USE THEREOF

(71) Applicant: Shandong D-Nutrimec Biomedical Co., Ltd., Heze (CN)

(72) Inventors: Zhidong Guo, Heze (CN); Jiajia Shao, Heze (CN); Hongwei Ma, Heze (CN)

(73) Assignee: Shandong D-Nutrimec Biomedical Co., Ltd., Heze (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/834,531

(22) PCT Filed: Dec. 26, 2023

(86) PCT No.: PCT/CN2023/141727
§ 371 (c)(1),
(2) Date: Jul. 30, 2024

(87) PCT Pub. No.: WO2024/212592
PCT Pub. Date: Oct. 17, 2024

(65) Prior Publication Data
US 2025/0257119 A1 Aug. 14, 2025

(30) Foreign Application Priority Data
Apr. 10, 2023 (CN) ......................... 202310368832.8

(51) Int. Cl.
*C07K 14/78* (2006.01)
*A61K 38/00* (2006.01)
(Continued)

(52) U.S. Cl.
CPC ............. *C07K 14/78* (2013.01); *C12M 21/02* (2013.01); *C12N 5/0037* (2013.01);
(Continued)

(58) Field of Classification Search
CPC ......... C07K 14/78; A61K 38/00; C12M 21/02
See application file for complete search history.

(56) References Cited

U.S. PATENT DOCUMENTS

2006/0258560 A1* 11/2006 Yang ..................... A61L 24/043
514/17.2

FOREIGN PATENT DOCUMENTS

| | | |
|---|---|---|
| CN | 101182355 A | 5/2008 |
| CN | 101501216 A | 8/2009 |

(Continued)

OTHER PUBLICATIONS

Kulvaniemi et al., 2019, Type III collagen (COL3A1): Gene and protein structure, tissue distribution, and associated diseases, Gene, 707: 151-171.*

(Continued)

*Primary Examiner* — Amber D Steele
(74) *Attorney, Agent, or Firm* — Thompson Coburn LLP; Steven M. Ritchey

(57) ABSTRACT

A recombinant humanized collagen type III alpha-1 (rhCol III α1), and an expression vector and use thereof are provided, relating to the technical field of bioengineering. A sequence on positions 154 to 1,221 of a human type III collagen α chain is ligated to an optimized vector pcDNA3.1, a resulting optimized expression vector is transfected into a human embryonic kidney cell Expi293F, and then rhCol III α1 is secreted to form a fusion protein with a soluble green fluorescent protein (GFP). The expressed rhCol III α1 that forms the fusion protein with the GFP shows an activity of promoting the migration of BALB/c (Continued)

3T3 cells, thus exhibiting a great application potential in the field of skin care.

2 Claims, 4 Drawing Sheets

Specification includes a Sequence Listing.

(51) Int. Cl.

| | | |
|---|---|---|
| *C12M 1/00* | (2006.01) | |
| *C12N 5/00* | (2006.01) | |
| *C12N 5/071* | (2010.01) | |
| *C12N 15/85* | (2006.01) | |

(52) U.S. Cl.
CPC ........... *C12N 5/0686* (2013.01); *C12N 15/85* (2013.01); *A61K 38/00* (2013.01); *C07K 2319/02* (2013.01); *C07K 2319/50* (2013.01); *C07K 2319/60* (2013.01); *C12N 2500/02* (2013.01); *C12N 2523/00* (2013.01); *C12N 2527/00* (2013.01); *C12N 2800/22* (2013.01)

(56) References Cited

FOREIGN PATENT DOCUMENTS

| CN | 103725622 | A | | 4/2014 | | |
|----|-----------|---|---|--------|---|---|
| CN | 103725623 | A | * | 4/2014 | | |
| CN | 108884441 | A | | 11/2018 | | |
| CN | 109988243 | A | | 7/2019 | | |
| CN | 110606896 | A | | 12/2019 | | |
| CN | 111417404 | A | | 7/2020 | | |
| CN | 116218864 | A | | 6/2023 | | |
| CN | 116333094 | A | | 6/2023 | | |
| WO | WO-2004028404 | A2 | * | 4/2004 | ........... | A61L 24/043 |
| WO | WO-2010021738 | A2 | * | 2/2010 | ............. | C07K 14/78 |
| WO | WO-2021150959 | A1 | * | 7/2021 | ............... | A61K 8/64 |

OTHER PUBLICATIONS

Sumiyoshi et al., 2006, Multifactor complex containing B element binding factor, BBF, and repressors regulate the human alpha 1 (III) collagen gene (COL3A1), Acta Medica Okayama, 60(3): 181-189.*
GFP_AEQVI seqeucne downloaded Aug. 6, 2025 from UniProt.*
Wilson et al., 1998, Bioluminescence, Annu. Rev. Cell Dev. Biol., 14: 197-230.*
Welsh et al., 1997, Reporter gene expression for monitoring gene transfer, Current Opinion in Biotechnology, 8: 617-622.*
English Translation of First Office Action issued for CN Application No. 202310055281.X, issued on Aug. 18, 2023.
English Translation of the First Office Action issued for CN Application No. 202310368832.8, issued on Aug. 12, 2023.
English Translation of the Second Office Action issued for CN Application No. 202310368832.8, issued on Oct. 17, 2023.

* cited by examiner

Coomassie
brilliant blue
staining

Coomassie
brilliant blue
staining

GFP-free collagen          GFP-fused collagen

RECOMBINANT HUMANIZED COLLAGEN TYPE III ALPHA-1, AND EXPRESSION VECTOR AND USE THEREOF

CROSS-REFERENCE TO RELATED APPLICATION

This patent application is a national stage application of International Patent Application No: PCT/CN2023/141727, filed on Dec. 26, 2023, which claims the benefit and priority of Chinese Patent Application No. 202310368832.8 filed with the China National Intellectual Property Administration on Apr. 10, 2023, the disclosure of which is incorporated by reference herein in its entirety as part of the present application.

REFERENCE TO SEQUENCE LISTING

A computer readable XML file entitled "GWPCTP20240403156-sequence listing.xml", which was created on Nov. 4, 2025, with a file size of about 10,580 bytes, contains the sequence listing for this application, has been filed with this application, and is hereby incorporated by reference in its entirety.

TECHNICAL FIELD

The present disclosure belongs to the technical field of bioengineering and specifically relates to a recombinant humanized collagen type III alpha-1 (rhCol III α1), and an expression vector and use thereof.

BACKGROUND

Collagen, as one of the most abundant proteins in mammals, accounts for 25% to 30% of total protein mass and is the main structural protein in the extracellular matrix found in various human connective tissues. Collagen participates in the composition of many human organ tissues, such as skin, cornea, neural retina, bones, and muscles. Collagen type III is one of the most abundant fibrillar collagens as well as a homotrimer formed by three a1(III) chains (Col3α1). Collagen type III in the skin gradually decreases with age, with a proportion from the fetal stage to the adult stage decreasing by 8% to 11%. Since being secreted by fibroblasts and other mesenchymal cell types, collagen type III becomes a major player in various inflammation-related pathologies. Collagen type III is involved in lung injury, viral and non-viral liver disease, renal fibrosis, hernia, and vascular diseases. Collagen type III and collagen type I are the major components of the interstitial matrix, and mutations in the collagen type III are associated with congenital connective tissue hypoplasia syndrome (also known as Ehlers-Danlos syndrome), vascular defects, and aortic aneurysms and aneurysms. In addition to its wide application in the field of skin care, collagen type III also has many exploratory studies that are expected to expand its cutting-edge applications. For example, biosynthetic corneas made from humanized collagen type III are optically clear and can replace donor therapy or genetically modified pig treatments without the need for immunosuppressive drugs. The humanized collagen type III can complete heart valve artificial synthesis and endometrial perfusion repair. Adding collagen type III to a tumor microenvironment can promote tumor cells to enter and maintain a dormant state, thus inhibiting tumor proliferation. Therefore, collagen type III shows a huge potential application market.

The collagen currently used in industry is mainly extracted from the skin or bones of pigs and cattle through acid, alkali, or enzymatic methods, or from the skin of deep-sea fish. Although the technology for extracting collagen from animal tissues is mature, there are problems such as immunogenicity and limited sources, making it difficult to meet the huge market demand. With the large-scale application of genetic engineering, the generation of recombinant collagen through genetic engineering has become the most promising method to solve the problem of limited collagen sources. Compared with animal-derived collagen, recombinant collagen has a short production cycle and low cost, is suitable for large-scale production, and can avoid problems such as animal protein immunogenicity and animal-derived diseases. Therefore, the preparation of recombinant collagen, especially recombinant humanized collagen, is currently a hot topic in collagen production research.

Full-length collagen has a large molecular weight (not less than 100 kDa) and exhibits a variety of protein post-translational modifications, such as proline and lysine hydroxylation as well as glycosylation. Currently, the domestic production of recombinant collagen type III uses an *Escherichia coli* expression system or a yeast expression system, and both of the expression systems have the advantage of large-scale expression. However, collagen obtained by the *Escherichia coli* expression system is mostly truncated, fragmented, or artificially modified based on the collagen sequence characteristics, and is quite different from the real collagen type III in the human body.

Meanwhile, since protein post-translational modification in yeast is different from that in the human body, recombinant collagen obtained by the yeast expression system is quite different from humanized collagen.

SUMMARY

In view of this, an objective of the present disclosure is to provide rhCol III α1, where the rhCol III α1 is fused with a green fluorescent protein (GFP) and has a desirable activity in promoting cell migration and a great application potential.

The objective of the present disclosure is also to provide an expression vector of the rhCol III α1, where sequence on positions 154 to 1,221 of a humanized collagen α chain is ligated to an optimized vector pcDNA3.1 to construct the expression vector capable of expressing the rhCol III α1.

The objective of the present disclosure is also to provide an expression method of the rhCol III α1, where an rhCol III α1 chain is expressed in a human embryonic kidney cell Expi293F, and a fusion expression plasmid is used to increase a protein expression level to realize the expression of a full-length segment of the rhCol III α1.

To achieve the above objective, the present disclosure provides the following technical solutions.

The present disclosure provides an rhCol III α1, where rhCol III α1 has the nucleotide sequence set forth in SEQ ID NO: 1.

The present disclosure further provides an expression vector for rhCol III α1, including the nucleotide sequence set forth in SEQ ID NO: 1, a gene sequence of a secretion signal peptide, a gene sequence of a GFP, and a DNA of a tobacco etch virus (TEV) protease digestion sequence.

Preferably, a preparation method of the expression vector includes the following steps: subjecting the nucleotide sequence set forth in SEQ ID NO: 1, the gene sequence of the secretion signal peptide, the gene sequence of the GFP, and the DNA of the TEV protease digestion sequence to codon optimization, and inserting a resulting synthesized gene between Nhe I and Xho I digestion sites of a plasmid pcDNA3.1 to obtain the expression vector, denoted as pcDNA3.1-GFP-CAL3α1.

More preferably, the secretion signal peptide is an α-mannosidase signal peptide.

The present disclosure further provides an expression method for rhCol III α1 fusion protein, including transfecting the expression vector into a human embryonic kidney cell Expi293F to allow expression.

Preferably, a culture method of the human embryonic kidney cell Expi293F includes the following steps: subjecting the human embryonic kidney cell Expi293F to pre-suspension culture in a serum-free medium on a shaker at 37° C. and 110 rpm with a humidity of 80% under 7% carbon dioxide.

Preferably, the transfecting is conducted when a resulting cultured human embryonic kidney cell Expi293F reaches a cell density of $(2.5\text{-}3.0)\times10^6$ cells/mL and a cell viability of greater than 95%.

The present disclosure further provides an rhCol III α1 fusion protein expressed by the expression method, where the rhCol III α1 fusion protein has an amino acid sequence set forth in SEQ ID NO: 3.

The present disclosure further provides the use of rhCol III α1 or the rhCol III α1 fusion protein in the preparation of a product for promoting a cell migration activity.

The present disclosure further provides the use of rhCol III α1 or the rhCol III α1 fusion protein in the preparation of a product for skin repair.

Compared with the prior art, the present disclosure has the following beneficial effects:

In the present disclosure, a gene sequence on positions 154 to 1,221 of a humanized collagen α chain is selected and ligated to a vector pcDNA3.1, the secretion signal peptide and GFP are added to the N-terminus of a target protein to optimize the expression vector. A resulting optimized expression vector is transfected into a human embryonic kidney cell Expi293F, and then rhCol III α1 is secreted to form a fusion protein with a soluble GFP. The fusion protein of the GFP and rhCol III has an activity of promoting the migration of α1 BALB/c 3T3 cells. Tests have shown that a 100 μg/mL recombinant collagen experimental group (scratch recovery rate 49%) shows significant activity in promoting the cell migration compared with a control group (scratch recovery rate 14%) after 6 hours of action. After 12 hours of action, the experimental group (100 μg/mL) shows a scratch recovery rate of 96%, which is much higher than the percentage of 38% in the control group. Activity studies have shown that the GFP-fused rhCol III α1 expressed in the present disclosure has desirable activity in promoting cell migration and exhibits a huge application potential.

DETAILED DESCRIPTION OF THE EMBODIMENTS

Figure 1:
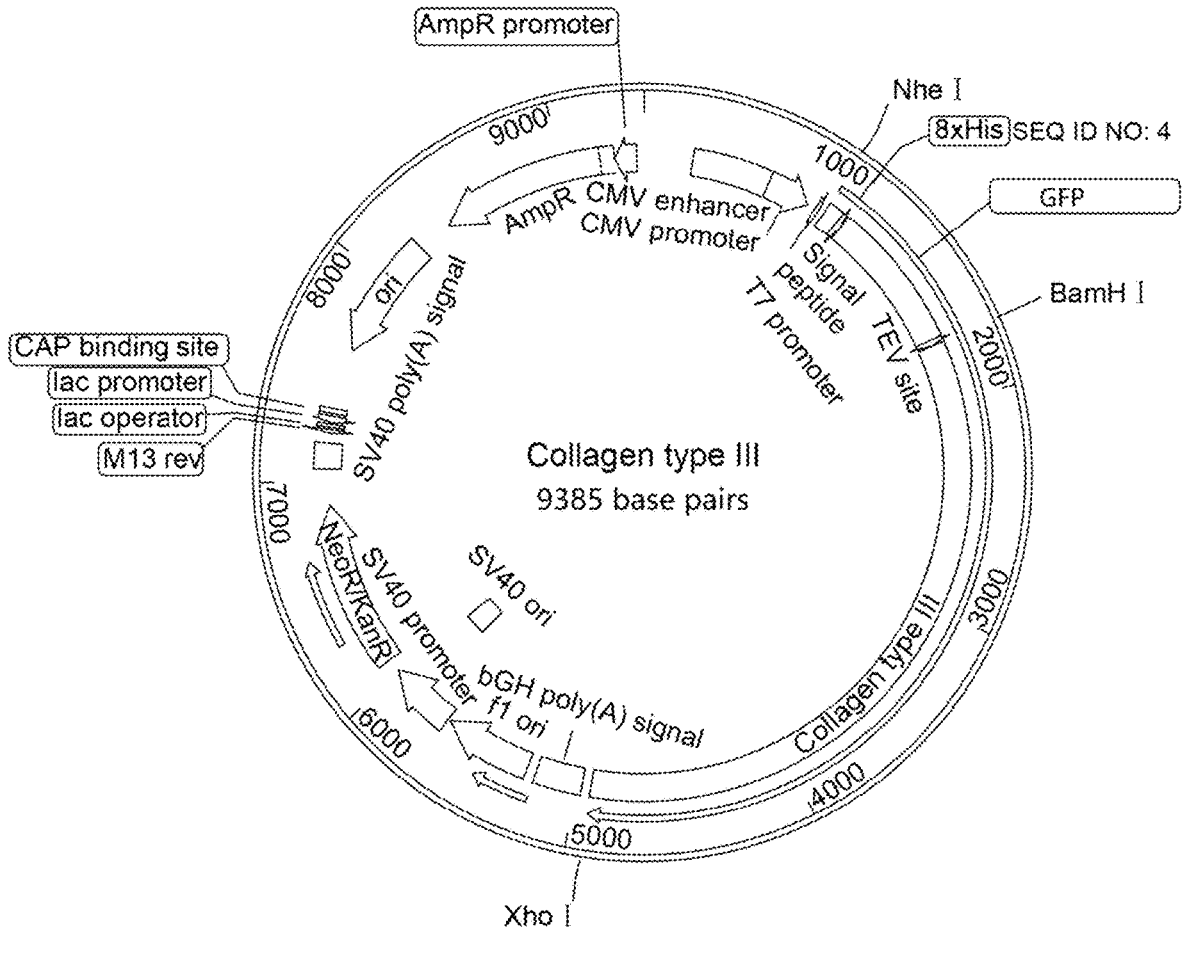
FIG. 1 shows a map of the expression vector of rhCol III α1-fused GFP.

The present disclosure provides rhCol III α1, where rhCol III α1 has the nucleotide sequence set forth in SEQ ID NO: 1. In the present disclosure, the nucleotide sequence of rhCol III α1 is subjected to codon optimization and then synthesized by Sangon Biotech Co., Ltd.

The present disclosure further provides an expression vector of rhCol III α1, including the nucleotide sequence set forth in SEQ ID NO: 1, a gene sequence of a secretion signal peptide, a gene sequence of a GFP, and a DNA of a tobacco etch virus (TEV) protease digestion sequence.

In the present disclosure, a preparation method of the expression vector includes the following steps: subjecting the gene sequence of the secretion signal peptide, the gene sequence of the GFP, and the DNA of the TEV protease digestion sequence to codon optimization, and inserting a resulting synthesized gene between Nhe I and BamH I digestion sites of a plasmid pcDNA3.1 to obtain an expression vector, denoted as pcDNA3.1-GFP; where the gene sequence of the secretion signal peptide, the gene sequence of the GFP, and the DNA of the TEV protease digestion sequence has a synthetic gene set forth in SEQ ID NO: 2. The gene sequence SEQ ID NO: 1 of rhCol III α1 is inserted between BamH I and Xho I digestion sites of the pcDNA3.1-GFP vector to obtain the expression vector capable of expressing a fusion protein of the GFP and rhCol III α1, denoted as pcDNA3.1-GFP-CAL3α1. The expression vector pcDNA3.1-GFP is synthesized by Sangon Biotech Co., Ltd. Expression of the GFP by a GFP gene can increase the expression level of the target protein. For the DNA of the TEV protease digestion sequence, the expressed TEV protease can recognize eight amino acid sequences. After being cleaved by the TEV protease, the GFP is released to obtain a GFP-free rhCol III α1.

In the present disclosure, the secretion signal peptide is an α-mannosidase signal peptide; the secretion signal peptide is synthesized by the company from the secretion signal peptide of α-mannosidase in *Trypanosoma cruzi*. Fusion of the secretion signal peptide in a plasmid of the pcDNA3.1 vector can help the recombinant protein expressed by the target gene to be secreted into a cell medium, thereby increasing the expression level of the recombinant protein. The secretion signal peptide can be cleaved by a signal peptidase after completion of expression.

The present disclosure further provides an expression method for rhCol III α1 fusion protein, including transfecting the expression vector into a human embryonic kidney cell Expi293F to allow expression. The human embryonic kidney cell Expi293F is derived from Thermo: a14528. The transfecting is conducted using a plasmid transfection kit derived from Beyotime: C0518.

In the present disclosure, a culture method of the human embryonic kidney cell Expi293F includes the following steps: subjecting the human embryonic kidney cell Expi293F to pre-suspension culture in a serum-free medium on a shaker at 37° C. and 110 rpm with a humidity of 80% under 7% carbon dioxide. The serum-free medium is derived from Genetimes ExCell Bio: HE000-N012.

In the present disclosure, the transfecting is conducted when a resulting cultured human embryonic kidney cell Expi293F reaches a cell density of $(2.5\text{-}3.0)\times10^6$ cells/mL and a cell viability of greater than 95%.

The present disclosure further provides an rhCol III α1 fusion protein expressed by the expression method, where the rhCol III α1 fusion protein has an amino acid sequence set forth in SEQ ID NO: 3.

The present disclosure further provides the use of rhCol III α1 or the rhCol III α1 fusion protein in the preparation of a product for promoting a cell migration activity. In the present disclosure, rhCol III α1 is subjected to cell migration activity assay. Assay results have shown that a 100 μg/mL recombinant collagen experimental group (scratch recovery rate 49%) shows significant activity in promoting the cell migration compared with a control group (scratch recovery rate 14%) after 6 h of action. After 12 hours of action, the experimental group showed a scratch recovery rate of 96%, which is much higher than the percentage of 38% in the control group. The GFP-fused rhCol III α1 expressed in the present disclosure has a desirable activity in promoting cell migration and exhibits a huge application potential, and exhibits a huge application potential in the preparation of a product that promotes cell migration activity.

The present disclosure further provides the use of rhCol III α1 or the rhCol III α1 fusion protein in the preparation of a product for skin repair.

The technical solutions provided by the present disclosure will be described in detail below with reference to the examples, but they should not be construed as limiting the claimed scope of the present disclosure.

Example 1 Constructing an Expression Vector of rhCol III α1

Sangon Biotech Co., Ltd. was entrusted to synthesize a gene sequence of a secretion signal peptide of α-mannosidase from *Trypanosoma cruzi*, a gene sequence of a GFP protein, and a DNA of a TEV protease digestion sequence, which were subjected to codon optimization, and a resulting synthesized gene was inserted between Nhe I and BamH I digestion sites of a plasmid pcDNA3.1 to obtain a GFP expression vector, denoted as pcDNA3.1-GFP. Sangon Biotech Co., Ltd. was entrusted to synthesize a DNA corresponding to an amino acid sequence (SEQ ID NO: 1) at positions 154 to 1,221 of a humanized collagen type III α1 chain, which was subjected to codon optimization, and a resulting synthesized gene was inserted between BamH I and Xho I digestion sites of the vector pcDNA3.1-GFP, and an expression vector capable of expressing a fusion protein of the GFP and rhCol III α1 was obtained, denoted as pcDNA3.1-GFP-CAL3α1 (FIG. 1).

The plasmid expression vector was transformed into *E. coli* DH5α, inoculated into an LB broth (each liter of the broth included 10 μg peptone, 5 μg yeast powder, and 10 μg NaCl), incubated at 37° C., 200 rpm for 2 hours, coated on an LB solid medium plate (0.1 mg/mL ampicillin), incubated upside down in an incubator at 37° C. for 12 hours, and a single colony was selected and added into 50 mL of LB broth (0.1 mg/mL ampicillin) to allow incubation at 37° C. and 200 rpm for 12 hours.

The plasmid was extracted with a plasmid bulk extraction kit (Beyotime: D0025-3), and a concentration of the expression vector was detected with a Nanodrop instrument. The expression vector could be stored at 4° C. for one month and was recommended to be used within a week.

Example 2 Expression and Purification of rhCol III α1

The Expi293F cells were subjected to pre-suspension culture in a serum-free medium on a shaker at 37° C. and 110 rpm with a humidity of 80% under 7% carbon dioxide. The plasmid transfecting was conducted when the cell density reached $(2.5-3.0)\times10^6$ cells/mL and a cell viability of greater than 95%. The transfection of the Expi293F cells was conducted with a plasmid transfection kit (taking 40 mL as an example): 80 μL of transfection reagent was added into 1 mL of cell medium, and mixed gently to obtain a solution A; 40 μg of plasmid extracted in Example 1 was added into 1 mL of cell medium, and mixed gently to obtain a solution B. The solution B was gently mixed with the solution A and allowed to stand for 15 min. The mixture of A and B was added to 40 mL of Expi293F cells obtained by the suspension culture, and the culture was continued for 6 days to 7 days, cell viability was checked every day, and the cells were collected when the cell viability was not more than 50%.

Figure 2:
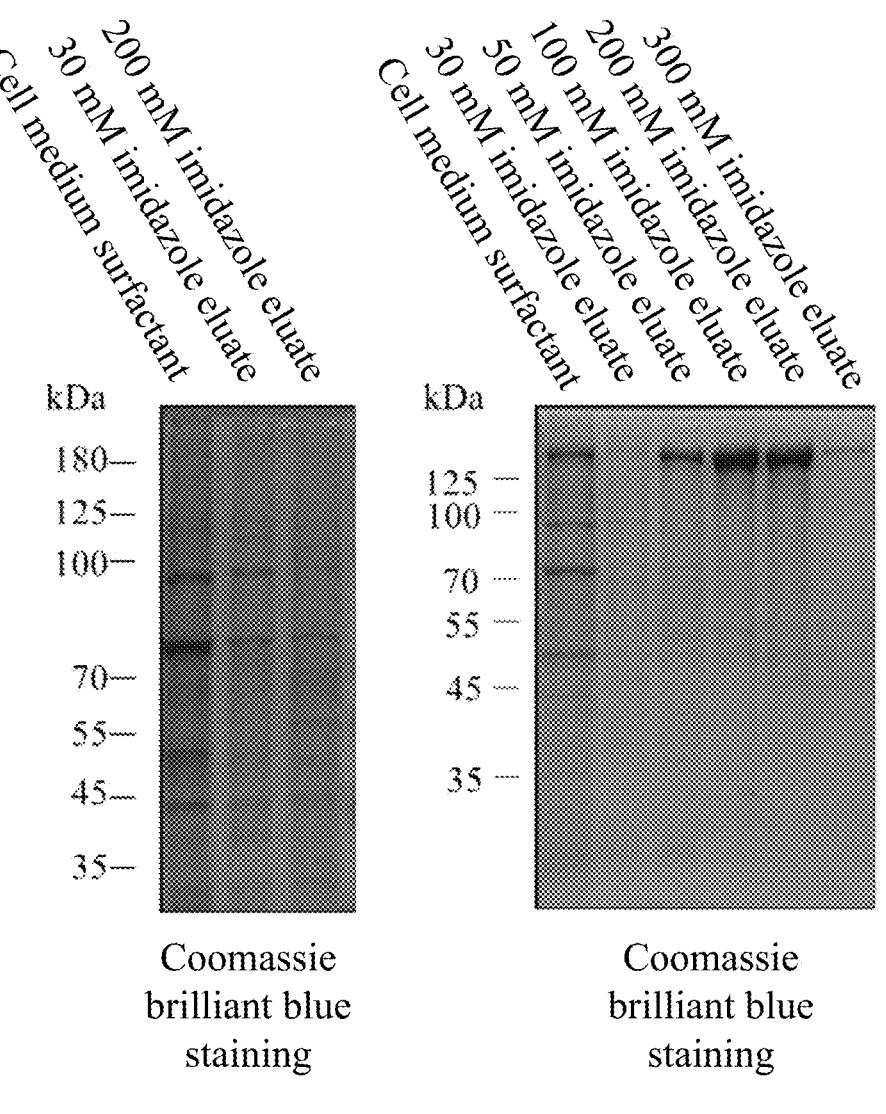
FIG. 2 shows an SDS-PAGE electrophoresis pattern of the rhCol III α1-fused GFP.
Figure 3:
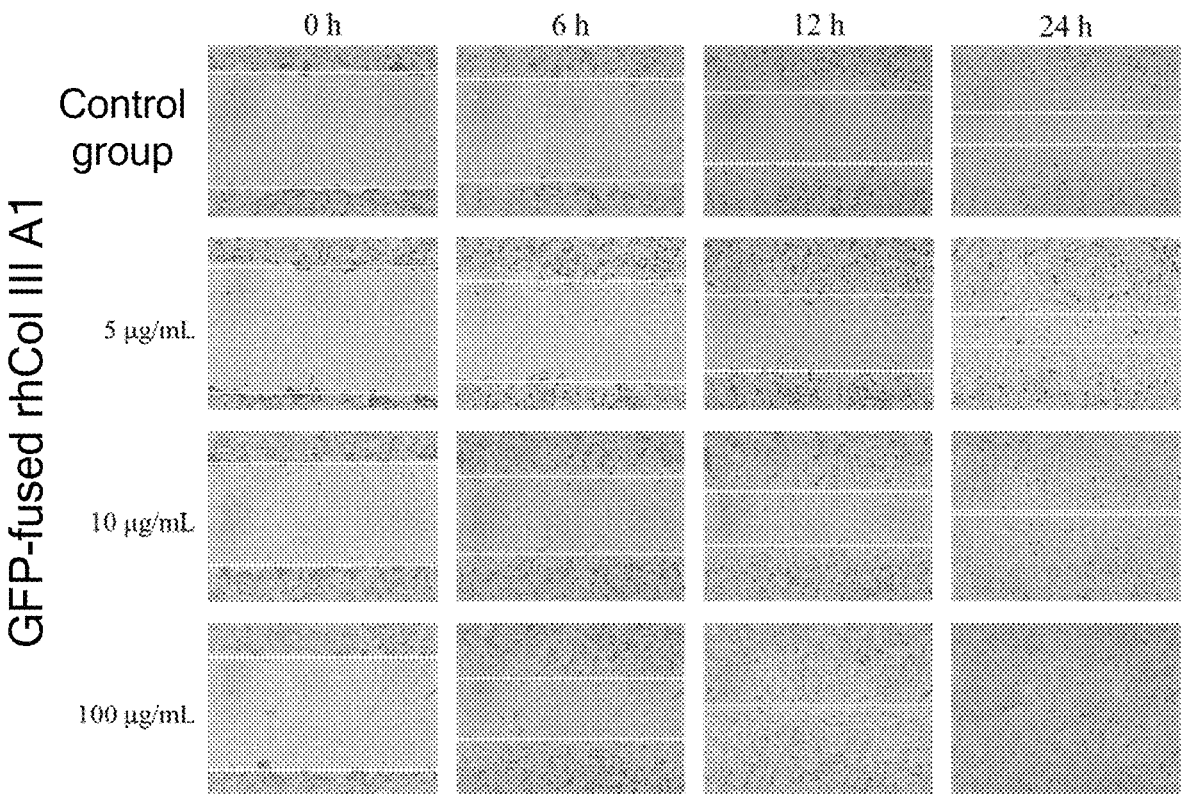
FIG. 3 shows experimental results of the rhCol III α1-fused GFP in promoting cell migration.

The resulting cell suspension was centrifuged at 11,000 rpm for 10 min at 4° C., an obtained supernatant was incubated with a well-balanced 5 mL nickel column (Thermo Fisher: 88221), eluted by gravity, the nickel column was washed with 50 mL of PBS solution containing 10 mM imidazole, gradient-eluted with PBS solutions containing 30 mM, 50 mM, 100 mM, 200 mM, and 300 mM imidazole separately, and the protein was detected by SDS-PAGE; obtained PBS elutions containing the target protein with high purity were combined, and the imidazole was removed by an ultrafiltration tube (Millipore, UFC9010), as shown in FIG. 2. As shown in FIG. 2, there was basically no collagen expression in the absence of GFP (left side). The GFP-fused expression vector had obvious bands when being expressed, a relatively pure fusion protein of the GFP and rhCol III α1 was obtained after purification on the nickel column. The results showed that the rhCol III α1 fusion protein obtained in the present disclosure had an expression level higher than that of the non-fusion protein.

Example 3 Determination of rhCol III α1 in Promoting Cell Migration Activity

Figure 5:
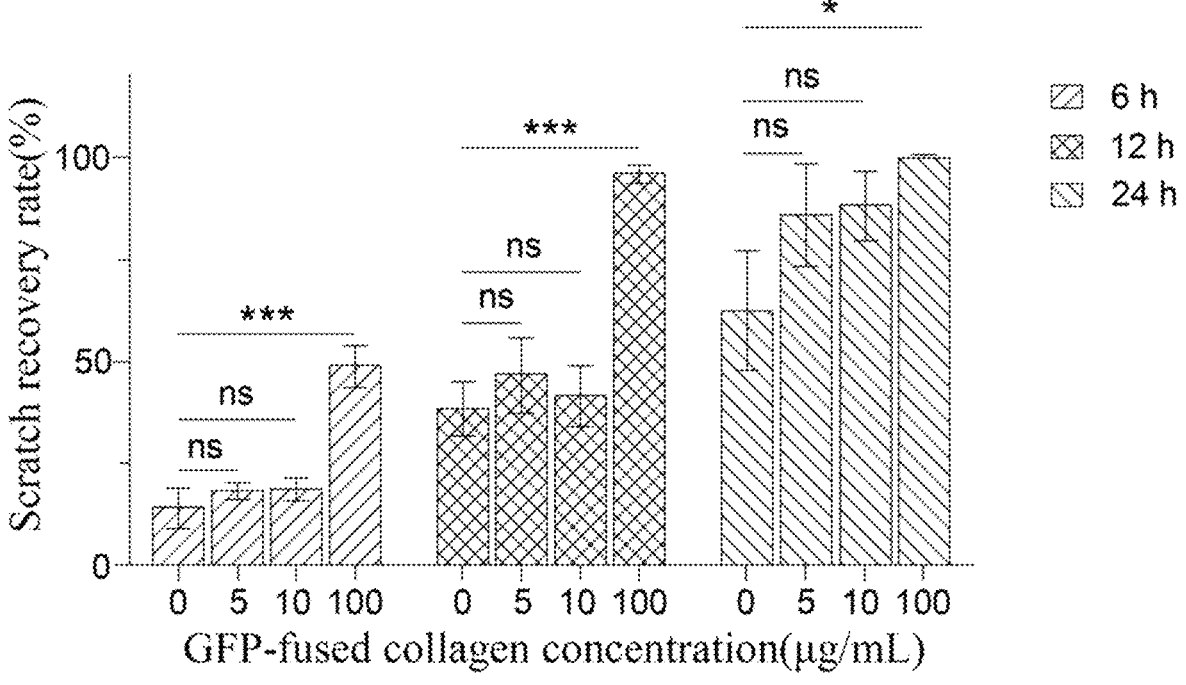
FIG. 5 shows a statistical graph of the scratch recovery rate of the rhCol III α1-fused GFP in promoting cell migration.

On the back of a 6-well plate, horizontal lines were evenly drawn with a marker using a ruler, where one horizontal line was drawn every 0.5 cm to 1 cm, and 5 horizontal lines were drawn for each well. About $5*10^5$ BALB/c 3T3 cells were added to each well and cultured overnight to make the cells adhere to the wall. The next day, the cells were streaked with a sterile tip using a ruler, and washed 3 times with PBS to remove the streaked cells; a DMEM medium (containing 1-2% FBS) was added to set up a control group (only adding PBS solution) and experimental groups with three concentrations of rhCol III α1 fusion protein (purified target protein in Example 2) of 5 μg/mL, 10 μg/mL, and 100 μg/mL, and the cells were returned to the incubator. Sampling and taking photos were conducted at 0 h, 6 h, 12 h, and 24 h. Three photos were taken for each experiment, and scratch areas were analyzed and calculated using software ImageJ to obtain the scratch recovery rate at different times. Recovery rate %=(scratch area at time 0—scratch area at a corresponding time)/scratch area at time 0*100. FIG. 5 showed the data of three independent experiments (mean±standard deviation), t-test, where P<0.05 was * (statistically significant difference), P<0.01 was , and P<0.001 was *.

As shown in FIG. 5, a 100 μg/mL recombinant collagen experimental group (scratch recovery rate 49%) showed significant activity in promoting the cell migration compared with a control group (scratch recovery rate 14%) after 6 hours of action. After 12 hours of action, the experimental group (100 μg/mL) showed a scratch recovery rate of 96%, which was much higher than the percentage of 38% in the control group.

According to the experimental steps of this example, the control group (only adding PBS solution), 15 μg/mL rhCol III α1 fusion protein (the purified target protein in Example 2), and 15 μg/mL rhCol III α1 were set up.

Figure 4:
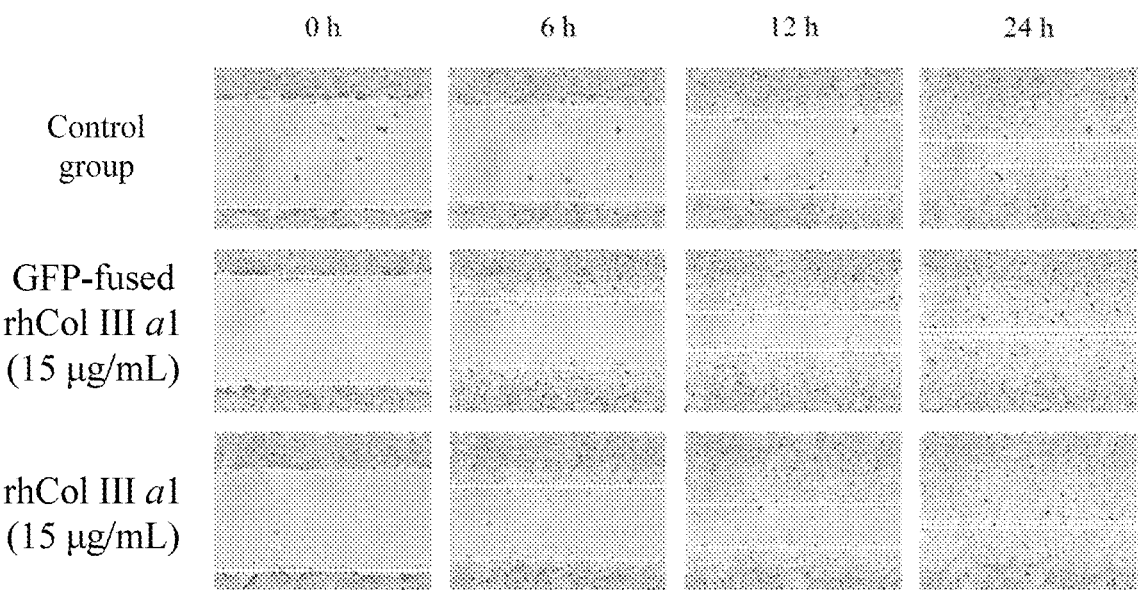
FIG. 4 shows the experimental results of rhCol III α1 and the rhCol III α1-fused GFP in promoting cell migration.

The fusion protein obtained in the present disclosure had comparable activity to the non-fusion protein after the excision of GFP (FIG. 4).

The above are merely preferred implementations of the present application. It should be noted that a person of ordinary skill in the art may further make several improvements and modifications without departing from the principle of the present application, but such improvements and modifications should be deemed as falling within the protection scope of the present application.

SEQUENCE LISTING

```
Sequence total quantity: 4
SEQ ID NO: 1               moltype = DNA  length = 3207
FEATURE                    Location/Qualifiers
source                     1..3207
                           mol_type = other DNA
                           note = nucleotide sequence of rhCol III a1
                           organism = synthetic construct
SEQUENCE: 1
caatacgaca gttatgatgt aaaaagtgga gtggcagttg gcggcctggc tggttacccg   60
gggccagcgg gaccaccggg cccgccgggt cccccgggta ccagcggcca ccctggaagc  120
ccgggcagtc cgggttacca gggtccgccc ggtgaaccgg gtcaagcagg tccgagcggc  180
cctcccggtc cgccgggtgc aatcggccct agcgggccgg ctggtaagga cggggagagc  240
ggtcgccctg gccgtccggg cgagccggc  ctgcccggcc ctccaggcat caaaggtccg  300
gcgggcattc cgggtttttcc gggtatgaaa ggccatcgtg gtttcgatgg tcgcaatggt  360
gagaaagggg agacgggtgc gcctggtctg aaaggcgaaa acggtctgcc gggcgagaac  420
ggagcgccgg gacctatggg tcctcgtggc gcgcaggtg  aacgcggccg cccggggctg  480
ccgggggcgg ctggtgcgcg tggcaacgat ggtgcgcgtg gctccgatgg ccaacctggc  540
ccgcccggac cacccggcac ggcaggtttt ccgggctcgc cgggcgcgaa aggcgaagtt  600
ggtccggcgg gtagcccagg ttctaatggc gcgccgggac aacgtgggga gccgggtccg  660
cagggccatg caggggcgca gggcccgcca ggaccgccgg ggatcaacgg tagccctggc  720
gggaagggcg agatgggtcc ggcagggatt ccgggagccc caggcctgat gggtgcccgc  780
ggacctcccg gtccggctgg ggccaatggt gcgcctggac tgcgtggtgg tgctggcgaa  840
ccgggaaaga atggtgcgaa aggcgagccg ggcccgccgg gcgaacgtgg tgaagctggt  900
atcccgggcg tgccgggtgc taaaggtgaa gatggcaagg acgggtcacc cggagaaccg  960
ggagcgaacg gattacctgg cgcggcggga gagagggcg  cgccagggtt tcgtggccca 1020
gcgggtccaa atggaatccc aggcgagaaa gggccggctg gagaacgtgg agcaccgggt 1080
ccagcgggcc cgcgtggtgc tgcgggcgaa ccggggcgtg acggtgtgcc gggcggtccg 1140
gggatgcgtg gcatgcctgg ttcgccggga ggcccgggtt ccgatggtaa accgggcccg 1200
ccaggcagtc agggggagtc cggacgtccg ggcccgccgg gaccatccgg tcctcgggga 1260
caaccgggag tgatgggctt cccgggtccg aaaggaaacg atggggcccc cggaaaaaac 1320
ggcgagcgtg gtggtccggg cggtccggga ccgcaaggac ctccggggaa gaacggtgaa 1380
accggtccgc aaggcccacc gggccctaca ggacctggag gcgataaagg tgacaccggc 1440
ccgccgggtc ctcaaggtct tcaggtctg  ccgggtacgg gcgggccacc tggcgagaat 1500
ggtaagccgg gtgaaccggg ccccaaggg  gacgccggtg cgccgggtgc acccggcggc 1560
aagggcgacg ctggcgcacc gggcgaaaga ggaccgccag gtttggcggg cgcgcccgga 1620
ctgcgtggcg gtgccggtcc accgggtccg gaaggtggca aaggcgctgc ggggccaccc 1680
gggcctccgg gcgcggcggg cactccgggt cttcagggga tgccgggcga gcgcggtggt 1740
ttgggttccc cgggtcccaa gggtgacaaa ggtgaaccgg gcggcccagg tgcagacggc 1800
gttccgggta aggacggtcc acgtggcccg accggtccta tcggccctcc tggccctgca 1860
ggtcagccgg gggataaggg cgaggtggt  gcgccaggac tgccgggtat cgcaggtccg 1920
cgtggttccc cgggcgagcg tggcgaaacc ggcccaccgg gacctgcggg ttttccaggt 1980
gcgcctggac aaaacgggga gccgggtggt aagggtgagc gtggcgcacc tggtgaaaag 2040
ggggaaggcg gccctccggg tgttgcgggc ccccgggg  gctcagggcc agctggccca 2100
ccgggcccgc agggtgtgaa aggagagaga ggttcgccgg gaggtcccgg tgccgccggt 2160
ttccctggcg cgcgtggatt gccgggaccg cctggtagca atggtaaccc gggcccgccg 2220
ggaccgagcg gttctccggg caaggacggt cctccgggcc cggccggtaa caccggtgcg 2280
cccgggtcgc cgggtgtcag cggccccaag ggcgatgcag gacaaccggg tgagaagggc 2340
tctccggggtg cgcaggcccc gccgggcgct ccgggaccgc tgggtattgc tggaattacc 2400
ggagcgcgtg gactggccgg tccgccgggt atgccgggc  cgcgcggcag cccagggcca 2460
cagggtgtga aaggcgagtc tggaaagccg ggtgcgaacg ggctgagcgg tgagcgcggg 2520
ccaccaggcc cgcaggtttt gccaggcctt gccggcaccg cgggagaacc ggggcgtgat 2580
ggaaatccgg gttctgatgg tctcccgggc cgtgatggtt ccccgggggg taagggcgac 2640
cgcggtgaga acggtagccc gggtgcgcca ggggcgccgg gtcaccctgg cccgccgggt 2700
cccgtcggtc cggcgggcaa aagcggtgac cgtggtgaga gcggtccggc ggggccggcc 2760
ggcgcgcctg gtccggcagg ctctcgtggt gcgccaggtc tcaaggccc  cagaggcgac 2820
aagggcgaaa ccggagaacg cggtgctgct ggcattaaag gtcatcgtgg cttcccgggt 2880
aacccaggcg cgccaggaag cccgggtccg gcagggcagc agggtgccat cggttctccg 2940
ggcccggcgg gtccgcgagg gccggttggc ccgagcggtc cgccgggtaa agacggcacc 3000
agcggtcacc cgggcccccat cggcccccgg ggtccgcgcg gtaatcgtgg cgaacgcgga 3060
tcggaaggtt ccccgggtca cccaggtcag cctgggccgc cgggtccgcc gggggctccg 3120
ggtccgtgtt gcggtggcgt tggggctgca gcgattgcag ggattggtgg ggagaaagca 3180
ggcggtttcg ccccttatta tggttaa                                     3207

SEQ ID NO: 2               moltype = DNA  length = 819
FEATURE                    Location/Qualifiers
```

```
source                  1..819
                        mol_type = other DNA
                        note = DNA of the TEV protease digestion sequence
                        organism = synthetic construct
SEQUENCE: 2
atgagactgc tgaccgccct gttcgcctac ttcatcgtgg ccctgatcct ggccttcagc   60
gtgtccgcca agagcatgca ccaccaccat caccatcatc acatgagcaa gggcgaggaa   120
ctgttcaccg gcgtggtgcc catcctggtg gaactggacg gcgacgtgaa cggccacaag   180
ttctctgtgc ggggcgaggg cgaggggggac gccacaaatg gcaagctgac cctgaagttc   240
atctgcacca ccggaaagct gcccgtgccc tggcctaccc tggtcacaac cctgacctac   300
ggcgtgcagt gcttcagcag ataccccgac cacatgaagc ggcacgattt cttcaagagc   360
gccatgcccg agggctacgt gcaagaacgg accatcagct tcaaggacga cggcacctac   420
aagaccagag ccgaagtgaa gttcgagggc gacaccctgg tcaaccggat cgagctgaag   480
ggcatcgact tcaaagagga cggcaacatc ctgggccaca agctggaata caacttcaac   540
agccacaacg tgtacatcac cgccgacaag cagaagaacg gcatcaaggc caacttcaag   600
atccggcaca acgtggaaga tggcagcgtg cagctggccg accactacca gcagaacacc   660
cccatcggcg acggccccgt gctgctgccc gacaatcact acctgagcac ccagagcgtg   720
ctgagcaagg accccaacga gaagcgggac cacatggtgc tgctggaatt tgtgaccgcc   780
gctggcatca cccacggcga gaacctgtac ttccaaggg                          819

SEQ ID NO: 3              moltype = AA  length = 1320
FEATURE                   Location/Qualifiers
source                    1..1320
                          mol_type = protein
                          note = amino acid sequence of the rhCol III a1 fusion
                           protein
                          organism = synthetic construct
SEQUENCE: 3
KSMHHHHHHH HMSKGEELFT GVVPILVELD GDVNGHKFSV RGEGEGDATN GKLTLKFICT   60
TGKLPVPWPT LVTTLTYGVQ CFSRYPDHMK RHDFFKSAMP EGYVQERTIS FKDDGTYKTR   120
AEVKFEGDTL VNRIELKGID FKEDGNILGH KLEYNFNSHN VYITADKQKN GIKANFKIRH   180
NVEDGSVQLA DHYQQNTPIG DGPVLLPDNH YLSTQSVLSK DPNEKRDHMV LLEFVTAAGI   240
THGENLYFQG GSQYDSYDVK SGVAVGGLAG YPGPAGPPGP PGPPGTSGHP GSPGSPGYQG   300
PPGEPGQAGP SGPPGPPGAI GPSGPAGKDG ESGRPGRPGE RGLPGPPGIK GPAGIPGFPG   360
MKGHRGFDGR NGEKGETGAP GLKGENGLPG ENGAPGPMGP RGAPGERGRP GLPGAAGARG   420
NDGARGSDGQ PGPPGPPGTA GFPGSPGAKG EVGPAGSPGS NGAPGQRGEP GPQGHAGAQG   480
PPGPPGINGS PGGKGEMGPA GIPGAPGLMG ARGPPGPAGA NGAPGLRGGA GEPGKNGAKG   540
EPGPRGERGE AGIPGVPGAK GEDGKDGSPG EPGANGLPGA AGERGAPGFR GPAGPNGIPG   600
EKGPAGERGA PGPAGPRGAA GEPGRDGVPG GPGMRGMPGS PGGPGSDGKP GPPGSQGESG   660
RPGPPGPSGP RGQPGVMGFP GPKGNDGAPG KNGERGGPGG PGPQGPPGKN GETGPQGPPG   720
PTGPGGDKGD TGPPGPQGLQ GLPGTGGPPG ENGKPGEPGP KGDAGAPGAP GGKGDAGAPG   780
ERGPPGLAGA PGLRGGAGPP GPEGGKGAAG PPGPPGAAGT PGLQGMPGER GGLGSPGPKG   840
DKGEPGGPGA DGVPGKDGPR GPTGPIGPPG PAGQPGDKGE GGAPGLPGIA GPRGSPGERG   900
ETGPPGPAGF PGAPGQNGEP GGKGERGAPG EKGEGGPPGV AGPPGGSGPA GPPGPQGVKG   960
ERGSPGGPGA AGFPGARGLP GPPGSNGNPG PPGPSGSPGK DGPPGPAGNT GAPGSPGVSG   1020
PKGDAGQPGE KGSPGAQGPP GAPGPLGIAG ITGARGLAGP PGMPGPRGSP GPQGVKGESG   1080
KPGANGLSGE RGPPGPQGLP GLAGTAGEPG RDGNPGSDGL PGRDGSPGGK GDRGENGSPG   1140
APGAPGHPGP PGPVGPAGKS GDRGESGPAG PAGAPGPAGS RGAPGPQGPR GDKGETGERG   1200
AAGIKGHRGF PGNPGAPGSP GPAGQQGAIG SPGPAGPRGP VGPSGPPGKD GTSGHPGPIG   1260
PPGPRGNRGE RGSEGSPGHP GQPGPPGPPG APGPCCGGVG AAAIAGIGGE KAGGFAPYYG   1320

SEQ ID NO: 4              moltype = AA  length = 8
FEATURE                   Location/Qualifiers
source                    1..8
                          mol_type = protein
                          organism = Homo sapiens
SEQUENCE: 4
HHHHHHHH                                                            8
```

What is claimed is:

1. A recombinant humanized collagen type III alpha-1 (rhCol III α1) fusion protein consisting of SEQ ID NO: 3 for use in a skin care product, the rhCol III α1 fusion protein being encoded by a fused nucleotide sequence, and wherein the fused nucleotide sequence comprises sequentially a gene sequence for encoding a secretion signal peptide, a gene sequence for encoding a 8× histidine tag, a gene sequence for encoding a green fluorescent protein (GFP), a DNA sequence for encoding a digestion sequence of a tobacco etch virus (TEV) protease, and a gene sequence for encoding rhCol III α1;

wherein the rhCol III α1 fusion protein has the amino acid sequence consisting of SEQ ID NO: 3; and wherein the gene sequence for encoding rhCol III α1 has the sequence consisting of SEQ ID NO: 1.

2. A product for skin repair, comprising the rhCol III α1 fusion protein according to claim 1 in the product for skin repair.

* * * * *